NICHOLAS & BLY.
Artificial Leg.
No. 1,510.
Reissued July 7, 1863.
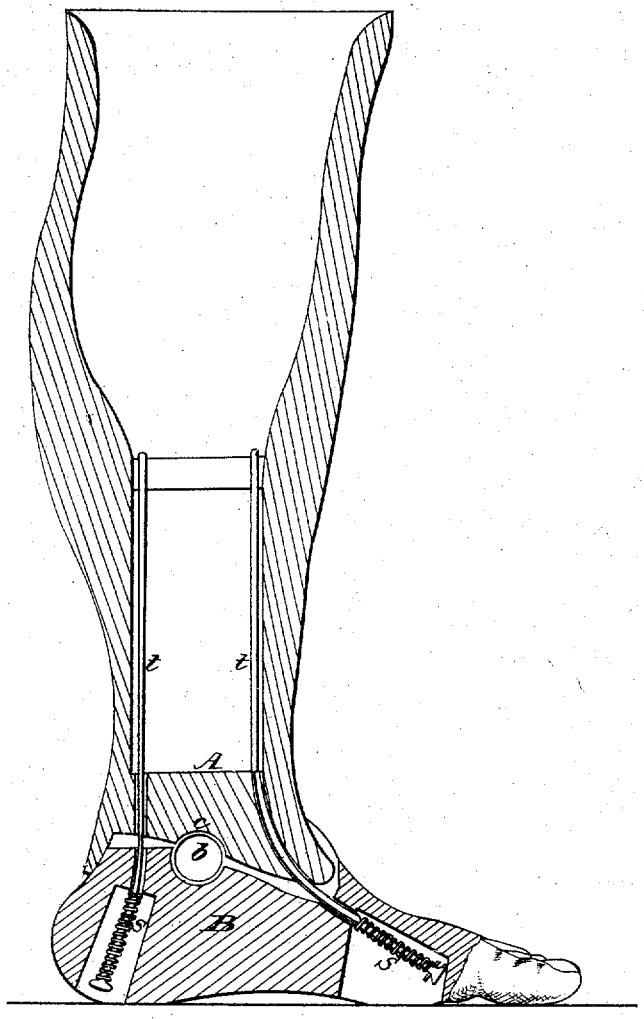
Witnesses
W. H. Smith
J. A. Phillips
Inventor.
Douglas Bly

UNITED STATES PATENT OFFICE.

DOUGLAS BLY, OF ROCHESTER, NEW YORK, ASSIGNEE OF R. H. NICHOLAS AND DOUGLAS BLY.

IMPROVEMENT IN ARTIFICIAL LEGS.

Specification forming part of Letters Patent No. 17,888, dated July 28, 1857; Reissue No. 1,510, dated July 7, 1863.

*To all whom it may concern:*

Be it known that R. H. NICHOLAS and DOUGLAS BLY, both of Rochester, in the county of Monroe and State of New York, did invent certain new and useful Improvements in the Construction of Artificial Limbs, for which Letters Patent of the United States were granted them on the 28th of July, 1857; and it is hereby declared that the following is a full and exact description thereof, reference being had to the accompanying drawings, making part of this specification.

This invention consists in the employment of a universal joint, which may in the artificial leg be substituted for any of the natural joints in the natural leg, and by which the elasticity and ease of motion of the limb are greatly increased.

In the drawings forming a part of this specification, the joint is shown adapted to the ankle, and consists of the ball *b* and cavities *c c*, forming the articulating surfaces of the ankle-joint.

This invention also consists in an arrangement of tendons and springs as follows: Tendons *t t* are provided for connecting the foot and leg, and with these tendons are connected springs *s s*, or their equivalents, to allow the necessary elasticity in the motions of the foot, and at the same time to hold the articulating surfaces of the joint in constant coaptation, to compensate for wear, to prevent rattling, and to retain the normal positions of the foot and leg.

In the old form of pin or bolt joint the foot is attached to the leg in a firm and rigid manner, and any side jerk—as, for instance, that produced by stepping upon an inequality in the surface of the ground—produces a severe shock, but by substituting a universal joint for the pin or bolt not only is the friction lessened, but a certain degree of elasticity is secured by which these objectionable shocks are avoided, and the foot is allowed to accommodate itself to inequalities in the ground and to grades or side hills, and thereby enables the wearer to walk on uneven surfaces; and it allows the wearer to flex the ankle in the line of motion like the natural ankle when walking with the toes turned outward to match the natural foot and to assume the varied positions necessary in labor. In fact, it allows every motion of the natural foot and leg with the minimum amount of friction, and at the same time combines remarkable lightness with great durability.

By this mode of constructing the joint the articulating surfaces perform another important function when in coaptation—viz., they retain the foot and leg in their normal relations to each other, as it is impossible for the leg or foot to slip or slide sidewise, or forward or backward, or in any other direction. Consequently, all the old cumbrous metallic fastenings are dispensed with.

It will be seen by the drawings that spherical bearings are employed between two portions of an artificial leg for the purpose of articulating the same. What is meant by spherical bearings is a convex and concave surface adapted to each other.

It is obvious that modifications may be made in the form of this joint, but modifications in form do not change or affect the general principle.

What is claimed as this invention, and desired to be secured by Letters Patent, is—

1. A universal joint in connection with two parts, A B, of an artificial leg, substantially as and for the purpose herein set forth.

2. The tendons *t t* and their springs *s s*, or their equivalents, in combination with two parts, A B, of an artificial leg, for the purpose of holding the said parts properly together and keeping the articulating surfaces of the joint in constant coaptation, substantially as herein specified.

In witness whereof I hereunto set my hand this 11th day of June, 1863.

DOUGLAS BLY,
*Assignee.*

Witnesses:
L. M. NEWTON,
JOSEPH DAWES.